US010685576B2

(12) United States Patent
Chapela et al.

(10) Patent No.: US 10,685,576 B2
(45) Date of Patent: Jun. 16, 2020

(54) AUGMENTED REALITY SYSTEMS BASED ON A DYNAMIC FEEDBACK-BASED ECOSYSTEM AND MULTIVARIATE CAUSATION SYSTEM

(71) Applicant: Suggestic, Inc., San Francisco, CA (US)

(72) Inventors: Victor Chapela, Palo Alto, CA (US); Ricardo Corral Corral, Mexico City (MX)

(73) Assignee: Suggestic, Inc., San Francisco, CA (US)

(*) Notice: Subject to any disclaimer, the term of this patent is extended or adjusted under 35 U.S.C. 154(b) by 221 days.

(21) Appl. No.: 15/858,713

(22) Filed: Dec. 29, 2017

(65) Prior Publication Data

US 2018/0190147 A1 Jul. 5, 2018

Related U.S. Application Data

(60) Provisional application No. 62/440,924, filed on Dec. 30, 2016, provisional application No. 62/440,982, (Continued)

(51) Int. Cl.
*G09B 5/02* (2006.01)
*G06N 3/04* (2006.01)
(Continued)

(52) U.S. Cl.
CPC .............. *G09B 5/02* (2013.01); *A23L 33/40* (2016.08); *A61B 5/0205* (2013.01); (Continued)

(58) Field of Classification Search
None
See application file for complete search history.

(56) References Cited

U.S. PATENT DOCUMENTS

2010/0331146 A1* 12/2010 Kil ..................... G06F 19/3481 482/8
2014/0100994 A1* 4/2014 Tatzel ................ G06Q 30/0268 705/27.1
(Continued)

OTHER PUBLICATIONS

Saul B. Needleman et al., "A general method applicable to the search for similarities in the amino acid sequence of two proteins," Journal of Molecular Biology 48, 1970, 8 pages.
(Continued)

*Primary Examiner* — Jason T Yen
(74) *Attorney, Agent, or Firm* — Carr & Ferrell LLP

(57) ABSTRACT

Augmented reality systems and methods for a decision augmentation system are provided. An example augmented reality system includes a ruleset generator system that creates rulesets based on empirical studies and a personalized program generation system that applies individualized data of a user to create a personalized program for the user based on one or more of the rulesets. In some instances a passive and active feedback system provides empirical results of actions and behaviors of the user and a multivariate causation system selectively adjusts the rulesets based on the empirical results of the actions and behaviors of the user. In various instances, a contextual filtering and adherence scoring system dynamically selects individualized suggestions according to context of the user and the personalized program for the user and provides augmented reality information overlays of the individualized suggestions.

20 Claims, 10 Drawing Sheets

Related U.S. Application Data filed on Dec. 30, 2016, provisional application No. 62/440,689, filed on Dec. 30, 2016, provisional application No. 62/440,801, filed on Dec. 30, 2016, provisional application No. 62/441,043, filed on Dec. 30, 2016, provisional application No. 62/441,014, filed on Dec. 30, 2016.

(51) Int. Cl.

| | |
|---|---|
| *G06N 3/08* | (2006.01) |
| *A23L 33/00* | (2016.01) |
| *G06N 20/00* | (2019.01) |
| *G06F 16/27* | (2019.01) |
| *G06F 16/901* | (2019.01) |
| *G06T 11/20* | (2006.01) |
| *G16H 50/20* | (2018.01) |
| *G16H 50/30* | (2018.01) |
| *G06N 5/02* | (2006.01) |
| *G06N 7/00* | (2006.01) |
| *A61B 5/0205* | (2006.01) |
| *A61B 5/00* | (2006.01) |
| *A61M 5/142* | (2006.01) |
| *G06F 1/16* | (2006.01) |
| *G06N 5/04* | (2006.01) |
| *G06T 11/60* | (2006.01) |
| *G09B 19/00* | (2006.01) |
| *G16H 20/60* | (2018.01) |
| *G06N 3/02* | (2006.01) |
| *G06T 19/00* | (2011.01) |
| *A61M 5/172* | (2006.01) |
| *A61B 5/021* | (2006.01) |
| *A61B 5/024* | (2006.01) |
| *A61B 5/08* | (2006.01) |
| *A61B 5/145* | (2006.01) |
| *A61B 5/1455* | (2006.01) |

(52) U.S. Cl.
CPC ............ *A61B 5/4806* (2013.01); *A61B 5/486* (2013.01); *A61B 5/4866* (2013.01); *A61B 5/681* (2013.01); *A61B 5/6803* (2013.01); *A61M 5/14244* (2013.01); *G06F 1/163* (2013.01); *G06F 16/27* (2019.01); *G06F 16/9024* (2019.01); *G06N 3/02* (2013.01); *G06N 3/0427* (2013.01); *G06N 3/0454* (2013.01); *G06N 3/08* (2013.01); *G06N 5/022* (2013.01); *G06N 5/025* (2013.01); *G06N 5/045* (2013.01); *G06N 7/005* (2013.01); *G06N 20/00* (2019.01); *G06T 11/206* (2013.01); *G06T 11/60* (2013.01); *G06T 19/006* (2013.01); *G09B 19/00* (2013.01); *G09B 19/0092* (2013.01); *G16H 20/60* (2018.01); *G16H 50/20* (2018.01); *G16H 50/30* (2018.01); *A23V 2002/00* (2013.01); *A61B 5/021* (2013.01); *A61B 5/02438* (2013.01); *A61B 5/08* (2013.01); *A61B 5/14532* (2013.01); *A61B 5/14551* (2013.01); *A61M 5/1723* (2013.01); *A61M 2005/14208* (2013.01)

(56) References Cited

U.S. PATENT DOCUMENTS

| | | | |
|---|---|---|---|
| 2015/0193853 A1* | 7/2015 | Ayzenshtat | G06Q 30/0631 705/26.7 |
| 2016/0035248 A1* | 2/2016 | Gibbs | G06T 7/0002 434/127 |
| 2018/0344239 A1* | 12/2018 | Blander | A61B 5/7264 |

OTHER PUBLICATIONS

Temple F. Smith et al., "Identification of Common Molecular Subsequences" Journal of Molecular Biology 147, 1981, 3 pages.

Chapela et al., "Augmented Reality and Blockchain Technology for Decision Augmentation Systems and Methods Using Contextual Filtering and Personalized Program Generation", U.S. Appl. No. 15/859,062, filed Dec. 29, 2017, pp. 1-77.

Chapela et al., "Deep Learning Ingredient and Nutrient Identification Systems and Methods", U.S. Appl. No. 15/859,126, filed Dec. 29, 2017, pp. 1-37.

Suppes, P., "A Probabilistic Theory of Causality", Amsterdam: North-Holland Publishing, ISBN0720424046, DOI: 10.1086/288485, 1970, 131 pages.

Cartwright, Nancy, "Causal Laws and Effective Strategies," Noûs, 13(4). DOI:10.2307/2215337, 1979, pp. 419-437.

* cited by examiner

FIG. 3

Admin Console demo v1.mov

00:28 ◁◁ ◁ ▷ ▷▷ -00:23

Suggested Production

| CPC | Programs | Dialogs | Ingredients | Users | Data | Customer Care |

◆ CPC

Active CPCs (Show inactive) [Check CPCs] [CDCDiabeticsPreventionDiet ▼] [Search] [Create New]

| Name | Program | FOR (User Segment) | IF (Action Rule Group) | THEN (Outcome) | Tags | | | Active |
|---|---|---|---|---|---|---|---|---|
| Consume less sugary snacks | CDCDiabeticsPreventionDiet | Everyone(All) | Eat less sugary snacks | Reduce obesity Indicators | CDC Diabetics Diet | Sugars [W] | | = 🖉 |
| Consume less whole milk | CDCDiabeticsPreventionDiet | Everyone(All) | Eat less whole milk | Reduce obesity Indicators | CDC Diabetics Diet | Pending [W] | Vegetarian [W] Whole milk | = 🖉 |
| Decrease consumption of fatty cuts of meat | CDCDiabeticsPreventionDiet | Everyone(All) | Eat less fatty meats | Reduce obesity Indicators | Saturated Fats [W] | | | = 🖉 |
| Decrease consumption of fried food | CDCDiabeticsPreventionDiet | Everyone(All) | Eat less fried foods | Reduce obesity Indicators | Transfats [W] | Saturated Fats | | = 🖉 |
| Decrease consumption of sugars | CDCDiabeticsPreventionDiet | Everyone(All) | Eat less sugar | Decrease Average Blood Sugar Level (ABC) | Decrease sugar [W] | | | = 🖉 |
| Decrease consumption of sugary snacks | CDCDiabeticsPreventionDiet | Everyone(All) | Eat less sugary snacks | Reduce obesity Indicators | Decrease sugar [W] | | | = 🖉 |
| Decrease consumption of whole milk products | CDCDiabeticsPreventionDiet | Everyone(All) | Eat less whole milk | Reduce obesity Indicators | [W] Wholemilk | | | = 🖉 |
| Decrease consumption of sodium | CDCDiabeticsPreventionDiet | Everyone(All) | Eat less salt | Reduce obesity Indicators | Salt | Sodium [W] | | = 🖉 |

| | | | | | | |
|---|---|---|---|---|---|---|
| Decrease consumption of Sugar Sweetened Beverages | CDCDiabeticsPreventionDiet | Everyone(All) | Decrease sweets | Reduce obesity Indicators | CDCDiabeticsPreventionDiet  Decrease sugar  Vegan  Vegetarian  W  Water | = 🖉 |
| Increase Consumption of beans | CDCDiabeticsPreventionDiet | Everyone(All) | Eat a variety of beans and peas | Reduce obesity Indicators | Dietaryfiber  plant-basedprotein  W | = 🖉 |
| Increase Consumption of dark green vegetables | CDCDiabeticsPreventionDiet | Everyone(All) | Eat a variety dark green vegetables | Reduce obesity Indicators | Dietaryfiber  W | = 🖉 |
| Increase Consumption of orange vegetables | CDCDiabeticsPreventionDiet | Everyone(All) | Eat a variety of orange vegetables | Reduce obesity Indicators | Dietaryfiber  W | = 🖉 |
| Increase Consumption of whole grains | CDCDiabeticsPreventionDiet | Everyone(All) | Eat more whole grains | Reduce obesity Indicators | Dietaryfiber  W  Whole grains | = 🖉 |
| Increase water uptake | CDCDiabeticsPreventionDiet | Everyone(All) | Increase water uptake | Lose weight | CDCDiabeticsPreventionDiet  RA  Water | = 🖉 |

Admin Console demo v1.mov

00:13 ◁▷ -00:38

| Suggested Production | | | | | | |
|---|---|---|---|---|---|---|
| CPC | Programs | Dialogs | Ingredients | Users | Data | Customer Care |

♦ Programs

Active Programs (Show Inactive)      +Create New

| Name | Author | Comment | Tags | | Active |
|---|---|---|---|---|---|
| ADADiet | American Diabetes Association | The mission of the American Diabetes Association (ADA) is to prevent and cure diabetes and to improve the lives of all people affected by diabetes. | ADADiet | = | ✎🗑 |
| AHADiet | American Heart Association | Suggetic — A diet based on The American Heart Association's Diet and Lifestyle Recommendation for a healthier heart. | ADADiet | = | ✎🗑 |
| CDC Diabetics Prevention Diet | Centers for Disease Control | A diet based on Centers for Disease Control's for diabetes prevention. | CDCDiabeticsPreventionDiet | = | ✎🗑 |
| CeliacDiet | Celiac Disease Foundation | Gluton is a type of protein found in grains such as wheat, barley, rye, and triticale. The Celiac Diet, which is used to treat celiac disease, excludes gluten in diet. | CeliacDiet | = | ✎🗑 |
| Chef Lol Greek Diet | Chef Maria Lol | The Greek or mediterranean Diet is know to be the healthiest diet in the world. Research shows that is linked to a reduction on the risk of diabetes, improving heart health, and sharpening the mind with foods rich in omega-3s. The Greek Diet is developed by world-renowned Greek Chef Maria Lol, and health journalist and former Olympic atheltete Sara Toland. | GreekDiet | = | ✎🗑 |
| Flexitarian Diet | Vegetarian Nutrition | The Flexitarian Diet is a type of vegetarian diet. A plant-based diet with the occasional meat item on the menu. This folks do their best to limit meat intake as much as possible and they have an almost entirely plant-based diet. | FlexitarianDiet | = | ✎🗑 |
| Genetic markers | The International Journal of Obesity | A single nucleotide polymorphian (SNP) is a variation in a single nucleotide that occurs at a specific portition in the genome. There are certain SNP's that are known to increase an individuals risk of being obese. | geneticmarkers | = | ✎🗑 |
| Lacto-ovo Vegetarian (inactive) | Vegetarian Nutrition | Lacto-ovo Vegetarian is a type of vegetarian. Lacto-ovo vegetarians do not consume red meat, white meat, fish or fowl. They do however consume dairy products and egg products. This is the most common type of vegetarian. | | = | ✎🗑 |
| Lacto Vegetarian (inactive) | Vegetarian Nutrition | Lacto Vegetarian is a type of vegetarian. Lacto vegetarians do not eat red or white meat, fish, fowl or eggs. They do however consume dairy products such as cheese, milk and yogurt. | Lactovegetarian | = | ✎🗑 |

500

Source Tag

| | | | |
|---|---|---|---|
| Low Carb Mediterranean | Nutrition Reviews | The key feature of the Mediterranean Diet is a carbohydrate restriction, which directly addresses impaired carbohydrate metabolism naturally. | [LowCarbMediterraneanDiet] = 🖉 |
| Low Fermantation Diet | Hamilton Health Sciences | The Low Fermantation Diet is used to treat irritable Bowel Syndrome (IBC). | [LowFermentationDiet] = 🖉 |
| Mediterranean Diet | Nutrition Reviews | The Mediterranean Diet is known to be the healthiest diet in the world. The diet emphasizes eating plant-based foods, such as fruits and vegetables, whole grains, legumes, and nuts. | [LowCarbMediterraneanDiet] = 🖉 |
| Ovo-Lacto Vegetarian Diet | American Journal of Public Health | An ovo-lacto vegetarian diet (or lacto-ovo vegetarian) does not include any meat, fish, or poultry, but does include some animal products such as milk, yogurt, and eggs. A typical ovo-lacto vegetarian diet can include fruits, vegetables, grains, legumes, nuts, seeds, flowers, herbs, fungi, milk, cheese, yogurt, kefir and eggs. | [VegetarianDiet] = 🖉 |
| | Vegetarian Nutrition | Ovo Vegetarian is a type of vegetarian. Ovo-vegetarians do not eat red or white meat, fish, fowl or diary products. They do however consume egg products. | [Ovovegetarian] = 🖉 |

500

*FIG. 5*
*(Cont'd)*

AUGMENTED REALITY SYSTEMS BASED ON A DYNAMIC FEEDBACK-BASED ECOSYSTEM AND MULTIVARIATE CAUSATION SYSTEM

CROSS-REFERENCE TO RELATED APPLICATIONS

The present patent application claims the benefit of U.S. Provisional Patent Application No. 62/440,924, filed Dec. 30, 2016, and titled "Personalized Program Generation System with Plan and Ruleset Stacking", U.S. Provisional Patent Application No. 62/440,689, filed Dec. 30, 2016, and titled "Dynamic and Feedback-Based Ecosystem", U.S. Provisional Patent Application No. 62/440,982, filed Dec. 30, 2016, and titled "Personalized Program Generation System with Adaptive Program Engine", U.S. Provisional Patent Application No. 62/440,801, filed Dec. 30, 2016, and titled "Contextual Filtering and Adherence Scoring Systems and Methods", U.S. Provisional Patent Application No. 62/441,014, filed Dec. 30, 2016, and titled "Deep Learning and Ingredient Identification Systems and Methods", and U.S. Provisional Patent Application No. 62/441,043, filed Dec. 30, 2016, and titled "Multivariate Causation Systems and Methods". The present patent application is related to Non-Provisional U.S. patent application Ser. No. 15/859,126, filed Dec. 29, 2017, and entitled "Deep Learning Ingredient and Nutrient Identification Systems and Methods". The present patent application is also related to Non-Provisional U.S. patent application Ser. No. 15/859,062, filed Dec. 29, 2017, and entitled "Augmented Reality and Blockchain Technology for Decision Augmentation Systems and Methods Using Contextual Filtering and Personalized Program Generation". All of the aforementioned disclosures are hereby incorporated by reference herein in their entireties including all references and appendices cited therein.

FIELD OF THE PRESENT TECHNOLOGY

The present technology relates to augmented reality systems based on a dynamic and feedback-based ecosystem that provides tailored solutions for users. The systems and methods provided herein comprise a plurality of individual feedback loops that provide users with adaptive health, wellness, productivity, activity and/or longevity programs that are being constantly adapted based on coded rulesets generated from empirical studies, personal biomarkers, genome, microbiome, blood test analysis, preferences, restrictions, beliefs and goals, as well as, sensor feedback, user feedback, external sources and input from multivariate causation analyses.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to various embodiments of the present disclosure include an augmented reality and decision augmentation system. The augmented reality and decision augmentation system includes a ruleset generator system that creates rulesets based on empirical studies and a personalized program generation system that applies individualized data of a user to create a personalized program for the user based on one or more of the rulesets. In some embodiments a passive and active feedback system provides empirical results of actions and behaviors of the user and a multivariate causation system selectively adjusts the rulesets based on the empirical results of the actions and behaviors of the user. According to some embodiments, a contextual filtering and adherence scoring system dynamically selects individualized suggestions according to context of the user and the personalized lifestyle and eating program for the user.

According to some embodiments of the present technology, the contextual filtering and adherence scoring system provides augmented reality information overlays and individual adherence scoring of individualized suggestions. In some instances, individualized suggestions help the user in selection of restaurant menu items, ingredients, beverages, food products, groceries, supplements, and medication. In various instances, the individualized suggestions use at least one of images, video streams, and contextual information from a computer system of the user.

Other example embodiments of the disclosure and aspects will become apparent from the following description taken in conjunction with the following drawings.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

FIG. 3 is a customizable graphical user interface for a ruleset generator system according to exemplary embodiments of the present technology.

FIG. 4 is another customizable graphical user interface for a ruleset generator system according to exemplary embodiments of the present technology.

FIG. 5 is another customizable graphical user interface for a ruleset generator system according to exemplary embodiments of the present technology.

DETAILED DESCRIPTION OF EXEMPLARY EMBODIMENTS

Figure 1:
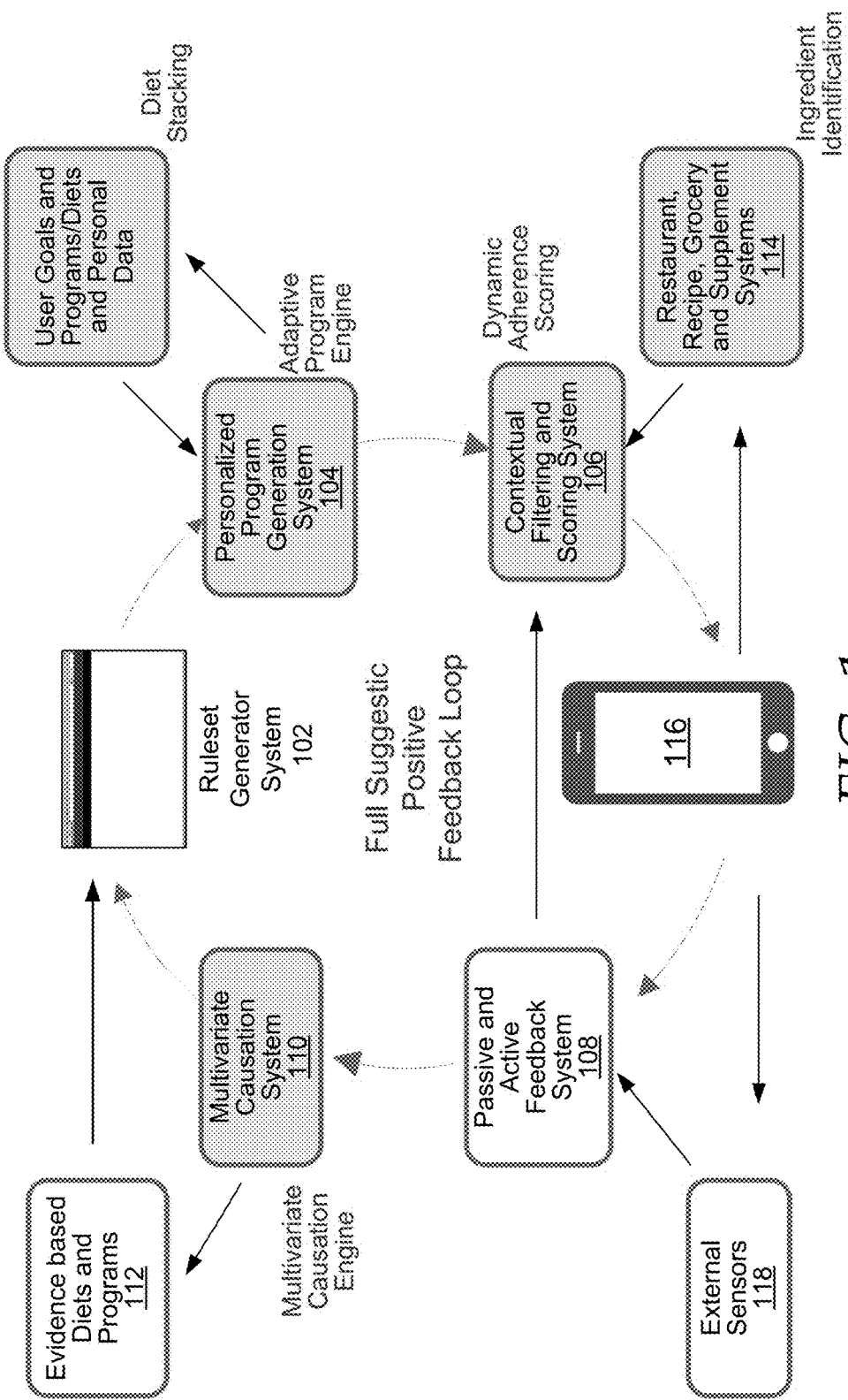
FIG. 1 illustrates an ecosystem according to exemplary embodiments of the present technology.

While the present technology is susceptible of embodiment in many different forms, there is shown in the drawings and will herein be described in detail several specific embodiments with the understanding that the present disclosure is to be considered as an exemplification of the principles of the present technology and is not intended to limit the technology to the embodiments illustrated.

FIG. 1 illustrates an example ecosystem 100 of the present disclosure. The ecosystem generally comprises a ruleset generator system 102, a personalized program generation system 104, a contextual filtering and adherence scoring system 106, a passive and active feedback system 108, and a multivariate causation system 110 (e.g. multivariate causation engine). These various systems can be executed using, for example, a server or within a cloud-based computing environment. In some embodiments, each of the various systems of the ecosystem 100 can be consolidated into a single system.

In various embodiments, the ruleset generator system 102 obtains input from two separate sub-systems. In some embodiments, the ruleset generator system 102 obtains lifestyle programs, dietary plans, nutrition plans, and empirical evidence-based programs (e.g. evidence based diets and programs 112) from various sources. For example, lifestyle and nutritional programs include peer-reviewed or other similar publications or data regarding diets and exercise such as ketogenic, paleo, vegan, low carbohydrate, low-fat, or even specific dietary plans such as Whole30®, the Daniel Diet, and so forth. The diets and programs (e.g. evidence based diets and programs 112) may be submitted directly by researchers, healthcare professionals, user groups or individual users. Further, the diets and programs (e.g. evidence based diets and programs 112) may be received by the ruleset generator system 102 and converted into rulesets that can be applied to a personal program for a user. For example, a ruleset can include rules for persons with specific biomarkers or characteristics, with specific ratios of macronutrients that are found in a particular dietary plan, as well as restricted or promoted food items.

According to various embodiments, the ruleset generator system 102 can also obtain input from the multivariate causation system 110, as will be described in greater detail below. In general, the multivariate causation system 110 can generate both updated lifestyle and nutritional programs from the various sources, as well as ruleset updates that are each based on output of the passive and active feedback system 108. In general passive feedback from sensors and external sources and active feedback from user input in the passive and active feedback system 108 is measuring empirical feedback from biometric resources or other applications that are tracking exactly how the user is behaving or acting based on the information given and plan established by the ecosystem 100. For example, if the user is following a prescribed plan that is designed to reduce weight but the user is not achieving results based on scale feedback received by the passive and active feedback system 108, the multivariate causation system 110 assess the lack of progress and determines a change to the ruleset(s) that might positively correlate with an improvement towards a goal. For example, if a user desires to lose weight and has not done so, the multivariate causation system 110 may discover that the user needs to potentially remove one or several food items from their diet, substitute one item for another, or change the order in which they consume different food types to improve the outcome for the user.

In various embodiments of the present disclosure, the multivariate causation system 110 utilizes artificial intelligence techniques such as deep learning or machine learning or big data that include information from other users having similar genetics, biomarkers, profile, activities, background, clinical data or other demographic or personal information. Thus, the user is not only analyzed in context of their own personal goals and personal information, but the multivariate causation system 110 can also derive or infer new rules based on what has worked or not worked for other similarly situated individuals. Some embodiments of the multivariate causation system 110 include any type of data streams or log data to derive or infer new rules based on sequences and patterns discovered. The sequence or log data can include, but is not limited to sensors, test results, biomarkers, activities, symptoms, supplements, medicine intake, food, beverages or locations. The multivariate causation engine can also determine the likelihood that each pattern or sequence of events will have a predicted outcome.

According to various embodiments, the personalized program generation system 104 can utilize ruleset stacking to create a converging solution for a set of dietary considerations and limitations for a user. For example, dietary considerations and limitations for a user may include being a vegetarian, being on a reduced-salt diet, and not liking certain gluten products. The personalized program generation system 104 can overlap these dietary considerations and limitations for a single user. In various embodiments the personalized program generation system 104 can overlap the dietary considerations and limitations of multiple users to create a single converging solution for multiple parties.

In some embodiments, the personalized program generation system 104 can also implement an adaptive program algorithm and create a personalized program for a user. The personalized program generation system 104 receives one or more rulesets that are applicable to the user based on information known about the user. For example, the user prefers a paleo diet. Thus, the personalized program generation system 104 will obtain rulesets for paleo adherents and will further personalize each of the rules based on the information of the user. The rulesets obtained from the ruleset generator system 102 can be selectively adjusted based on other information such as user goals, user programs/diets, and personal data of the user. For example, personal data of the user may include their; genetic information, microbiome, biomarkers, clinical, medical or health data, activities, age, weight, height, ethnic background, other demographic information, and so forth.

In various embodiments, the personalized program generation system 104 can implement a data gathering process whereby a user takes or uploads lab tests, fills in a questionnaire or shares information by other means to select any appropriate ruleset and goal for the user. To be sure, this can be augmented with more detailed information about the user such as specific objective and subjective demographic information, genetic test information, microbiome testing, and so forth. This information can also be obtained from medical records, including electronic medical records. An example method for collecting user information comprises the use of a chatbot that is programmed to interact with a user to request diet preferences and health conditions, as well one or more target goal(s). Another example is to obtain permission of the user to connect to their health application, health lab test, device or third-party services that will further enhance the personalization of their program.

Accordingly to embodiments of the present disclosure, the contextual filtering and adherence scoring system 106 is configured to execute dynamic adherence scoring algorithms to determine the adherence level of any meal or activity against the personalized program, diet or plan. The contextual filtering and adherence scoring system 106 obtains information from external and internal sources such as restaurant, recipe, grocery and supplement systems 114 or databases. In some embodiments, the contextual filtering and adherence scoring system 106 obtains recipe, supplement, grocery, and restaurant menu information using deep learning and artificial intelligence information gathering techniques. The contextual filtering and adherence scoring system 106 also obtains feedback on these types of information from user interaction with the ecosystem 100. This user feedback assists in resolving errors or inconsistencies with data.

According to some embodiments, the contextual filtering and adherence scoring system 106 can use specific techniques to examine menus, recipes, and ingredient lists from a wide variety of sources and correlate and harmonize what is known about individual meals, activities or places. In this way, the contextual filtering and adherence scoring system 106 can select appropriate meals or activities for the user based on their goals and personalized program.

In various embodiments, the contextual filtering and adherence scoring system 106 provides personalized programs to the user through the computing device 116. The contextual filtering and adherence scoring system 106 provides the user with a personalized program that is tailored based on selection of empirical lifestyle and nutritional programs that are converted to rulesets and applied to a goals, preferences, and demographics of the user. Contextual filtering is applied in some embodiments to selectively tailor the recipe or menu suggestions provided to the user in accordance with their personalized plan generated by the personalized program generation system 104.

In some embodiments, the computing device 116 executes a client side application that provides personalized plans and receives both passive and active feedback, in some embodiments. For example, computing device 116 may be the computer system shown in FIG. 8.

In various embodiments, the passive and active feedback system 108 receives data from the user through the computing device 116. For example, the user may create a food log or record their exercise activity. The user can also take pictures of food, menus, ingredient lists, and so forth. This information may be fed back into the restaurant, recipe, grocery and supplement systems 114 or databases. This gathered information can also be redirected back to the passive and active feedback system 108 for further analysis by the multivariate causation system 110.

In some embodiments, the passive and active feedback system 108 collects information from external sensors 118. For example, external sensors 118 include wearables (e.g., smart glasses, watches, etc.), sleep sensors, blood pressure monitors, glucose monitors and insulin pumps, blood pressure sensors, respiration monitors, pulse-oximetry meters, heart rate meters, and so forth—just to name a few.

In various embodiments of the present technology, the multivariate causation system 110 is configured to receive empirical feedback about the user and their behavior from the computing device 116 and the external sensors 118. The multivariate causation system 110 uses the specific information known about the user and those users that are similar to the user in in one way or another. For example, similarities may include goals, biometrics, biomarkers, genetics, demographics, lifestyle, and so forth. The multivariate causation system 110 further uses feedback from the external sensors 118 to selectively modify how a diet of the user is prioritized and if rulesets are adjusted for the user. For example, as different users progress towards a goal, their passive and active feedback is analyzed by the multivariate causation system 110 to determine what has worked for the users. The multivariate causation system 110 then modifies and reprioritizes the program rulesets so that the patterns and activity sequences that work best are suggested, and those patterns or sequences that do not work are reduced or avoided. The multivariate causation system 110 can adjust priority and/or rules for the diets and programs to more closely align with the goals of the successful users. The multivariate causation system 110 receives streams of data from user passive and active feedback, as well as the programs, goals and personal data and adjusts the rulesets dynamically or periodically.

In some embodiments, the multivariate causation system 110 can also act as a data producing system that reports back information for use in the lifestyle and nutritional programs (e.g. evidence based diets and programs 112) from various sources. The multivariate causation system 110 can deeply analyze user feedback and determine specific variations on behaviors and determine how they affect the desired outcomes. For example, the multivariate causation system 110 may determine that the user moves closer to achieving a goal when they restrict carbohydrate consumption in the morning and evening, or if they eat vegetables as snacks as opposed to combining them with protein sources.

Figure 2:
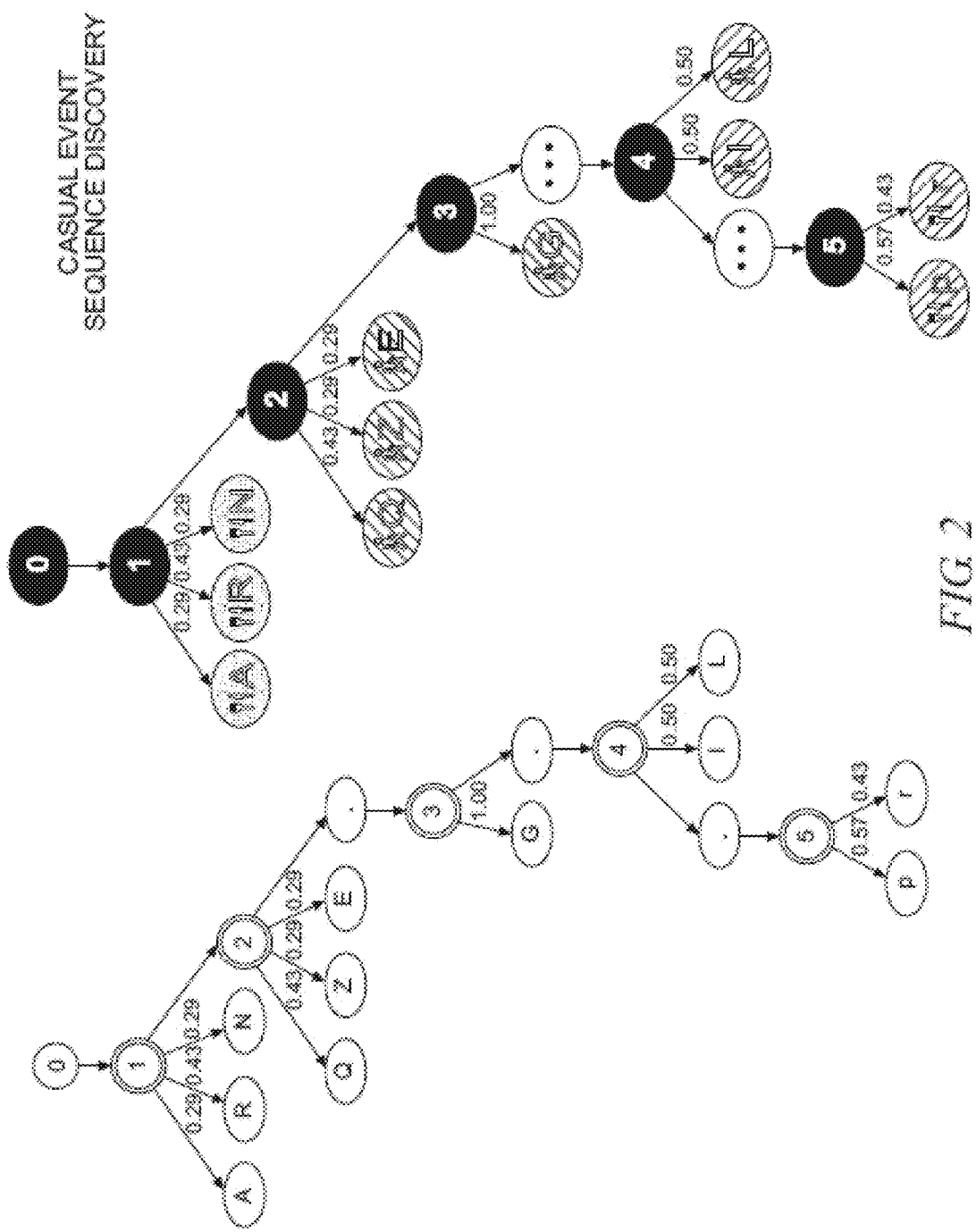
FIG. 2 shows a causation event sequence performed by a multivariate causation system according to exemplary embodiments of the present technology.

FIG. 2 illustrates an example causation event sequence 200 performed by the multivariate causation system 110. The causation sequence 200 (e.g. causal event sequence discovery) is a process performed from events gathered from user behaviors, the external sensors 118, and the computing device 116. Other example methodologies that can be implemented by the multivariate causation system 110 are described with further details in FIG. 6 (e.g. low entropy approaches for causal inference). In some embodiments, the multivariate causation system 110 can generate states compatible with the output of a deep multi-label, multi-ontology, and multi-model network architecture as described in Non-Provisional U.S. patent application Ser. No. 15/859,126, filed Dec. 29, 2017, and entitled "Deep Learning Ingredient and Nutrient Identification Systems and Methods", which is incorporated by reference herein in its entirety, including all references cited therein. In various embodiments, the multivariate causation system 110 personalizes programs as described in Non-Provisional U.S. patent application Ser. No. 15/859,062, filed Dec. 29, 2017, and entitled "Augmented Reality and Blockchain Technology for Decision Augmentation Systems and Methods Using Contextual Filtering and Personalized Program Generation", which is incorporated by reference herein in its entirety, including all references cited therein.

In various embodiments of the present technology, systems of the ecosystem 100 work together in a collective and synergistic manner to provide a user with lifestyle and nutritional plans for improving their health. The ecosystem 100 uses various feedback loops (represented by the individual systems of the ecosystem 100) to create an environment that learns based on empirical feedback and fine tunes a plan for a user based on this information.

Referring back to the multivariate causation system 110, in some embodiments the multivariate causation system 110 is configured to receive input from a plurality of different types of external sensors (e.g. external sensors 118) as well as the computing device 116 of the user. For example, the user may be a diabetic that uses a continuous glucose monitor and an insulin pump. The user may also use a wireless scale, a smart watch, and other similar devices. The data from external sensors 118 may also include location, mood, temperature, biomarkers and any sensor generated data. External sensors 118 provide input into the multivariate causation system 110. In some embodiments, a portion of the external sensors 118 provide data to a third-party such as a proprietary system or health professional. For example, the continuous glucose monitor for the user may transmit signals back to a physician of the user or to a monitoring service. These third-party services may compute various metrics regarding insulin pump operations. Each external sensor can transmit data for further processing that is not performed within the ecosystem 100. The third-party analysis can be provided back to the ecosystem 100, and specifically the multivariate causation system 110. Thus, the multivariate causation system 110 can receive raw or processed data from the external sensors 118 or from additional third-party processors that generate more complex metrics from the external sensor signals.

In various embodiments, input is received from the computing device 116. For example, the user may utilize the computing device 116 to obtain pictures or video of food consumed, as well as a food or activity log kept by the user. In another example embodiment, an external sensor can include smart glasses that capture video and audio periodically or continuously. The captured video and audio tracks food consumed as well as activities for the user. This tracking information is gathered over time so that food consumption patterns such as an order of food consumed, as well as a time and speed consumed may be recorded within any convenient detail level. Other activities and states of the user such as exercise, sleep, and mood may also be recorded and logged.

As mentioned above, according to various embodiments the multivariate causation system 110 uses three types of data including external data sources such as lab tests or inferred biomarkers, passive feedback such as data streams from sensors, and active feedback such as user logging food and activities through their computing device (e.g. computing device 116). An example collection of active and passive data includes, but is not limited to empirical data such as how well the user sleeps, what the user ate, how the user moves and exercises, where he is all with regard to time and sequences of actions. For example, a question to consider is whether the user exercises in a fasted state and consumes protein within an hour of working out in the morning. This individual may lose weight faster than a bio-similar person who consumes carbohydrates before working out and does not have protein after their workout.

In various embodiments, the multivariate causation system 110 is configured to coalesce these wide ranging and multi-faceted analyses and create new potential rules, rulesets and/or data for use in empirical studies. The output generated by the multivariate causation system 110 can be associated with other users who have similarities such as demographic, genetic, microbiome or others. Thus, as users participate and provide the multivariate causation system 110 with active and passive data, the multivariate causation system 110 can begin to assess successful and unsuccessful behaviors for that individual, which is likely to be predictive of the success or failure of other similar users. The multivariate causation system 110 can utilize the active and passive data of many users to determine recommendations or suggestions for changes to rulesets that, if enacted by this group of users would result in users achieving a stated goal. Again, this process is conducted within the context of a specific goal or set of goals. The achievement of the goal(s) is improved by determining what works for similar genetically, demographically, contextually, and biosimilar users. This close monitoring of actual results of actions and dietary behaviors of similar users provides context for these contextually similar users. That is, when users with similar genetics act in similar ways with respect to their diet and exercise, it can be assumed that the users are expressing their genes differently from one another. The system can look for commonalities between users that are not responding to personalized diet and exercise plans and determine potential changes to rulesets for these individuals so as to improve their outcome. Because of the continuous monitoring of active and passive feedback, changes in response for the user are tracked and additional changes can be made to their diet and activities if goals are still not being met.

According to various embodiments, these processes can also aid in the identification of medical issues such as hypothyroidism and other underlying medical conditions that hinder weight loss and promote weight gain. For example, if a user is biosimilar to other users that are all losing weight and the user is following the same plan but not losing weight, the multivariate causation system 110 may identify that a body temperature of the user is always low. This low body temperature may indicate that the user has a potential thyroid deficiency. Furthermore, the multivariate causation system 110 may alert the user that a medical evaluation may be necessary.

In various embodiments, the multivariate causation system 110 can also find and extract the sequence of events that lead to a specific user or group of similar users to achieve an expected goal. This sequence of events can be generated as a Hidden Markov Model output. For example, FIG. 2 illustrates the causation event sequence 200 performed by the multivariate causation system 110. Furthermore, another example methodology for finding event sequences that can be implemented by the multivariate causation system 110 is described in FIG. 6.

According to some embodiments, the multivariate causation system 110 helps a user find gaps or differences in their plan relative to others who have been successful. For example, a user may be encouraged to walk an extra 30 minutes per day based on empirical results received from other similar users with the same diet plan and/or goal. If these similar other individuals are determined to have walked more than the user, then the user is failing. Thus, the user is encouraged to increase exercise activity through the application on their computing device (e.g. computing device 116). The user is then tracked through their wearables to ensure that this goal to increase exercise is being accomplished.

According to various embodiments, the change or changes to a personalized plan can be a result of an augmented ruleset that is generated based on empirical results of the user. Thus, if it is determined that other users that are similar to the user have only been successful when eating certain combinations of food, the ruleset for this group can be updated to include these specific combinations of food. Thus, the multivariate causation system 110 allows the ecosystem 100 to improve its predictions and suggestions over time as feedback from users is received and analyzed.

Figure 3:
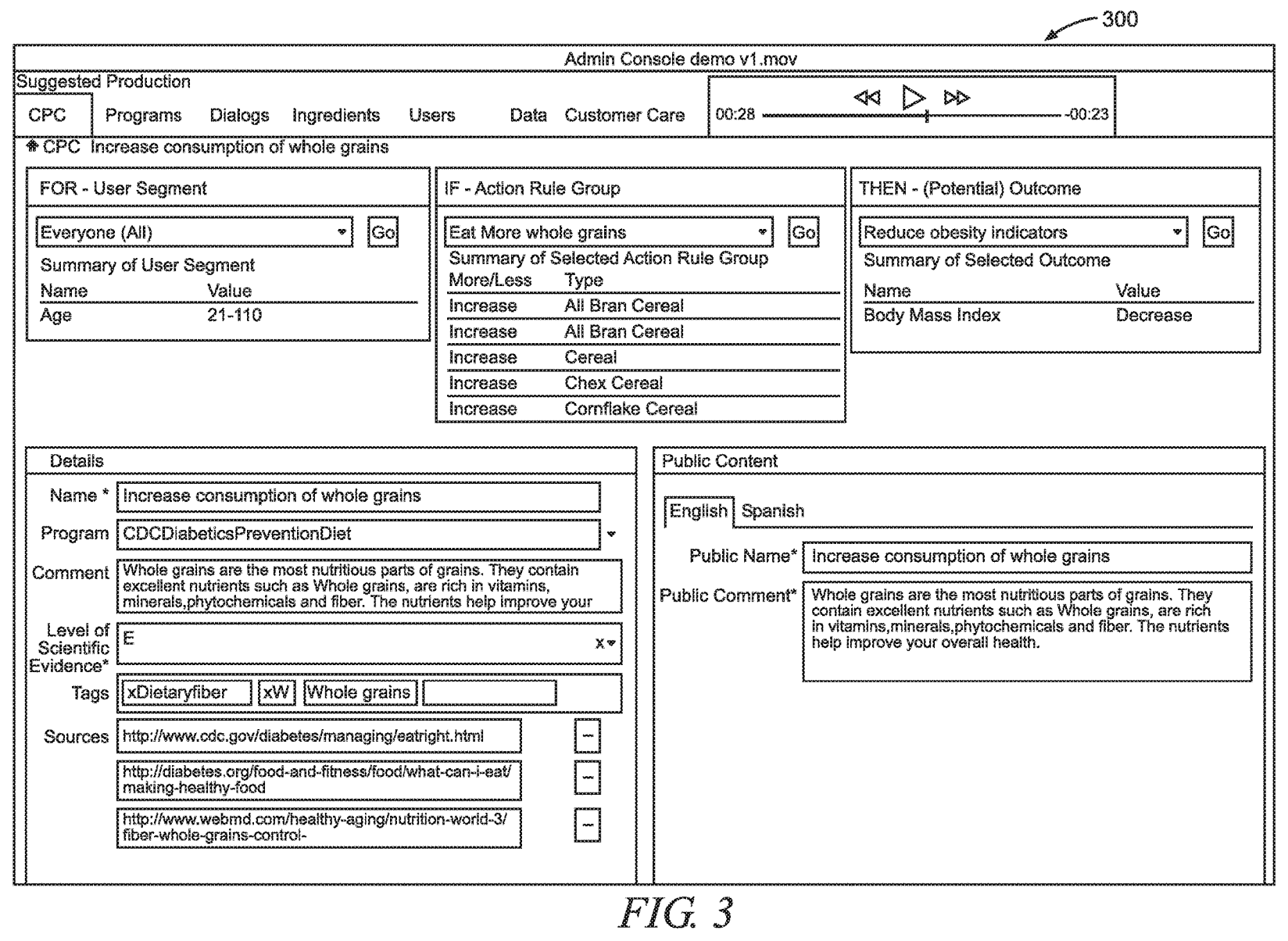

FIG. 3, FIG. 4, and FIG. 5 are customizable graphical user interfaces 300, 400, and 500, respectively, which enable the ruleset generator system according to exemplary embodiments of the present technology. FIG. 3, FIG. 4, and FIG. 5 illustrate customizable graphical user interfaces 300, 400, and 500, respectively, used for the creation of rulesets based on empirical data and the applicability of a ruleset to a given individual (based on ethnicity, genetics, or other categories). Additionally the graphical user interfaces show specific cause and effect scenarios such as "if a certain action is taken", a "beneficial result(s)" will occur based on the behavior for that particular type of individual.

Figure 6:
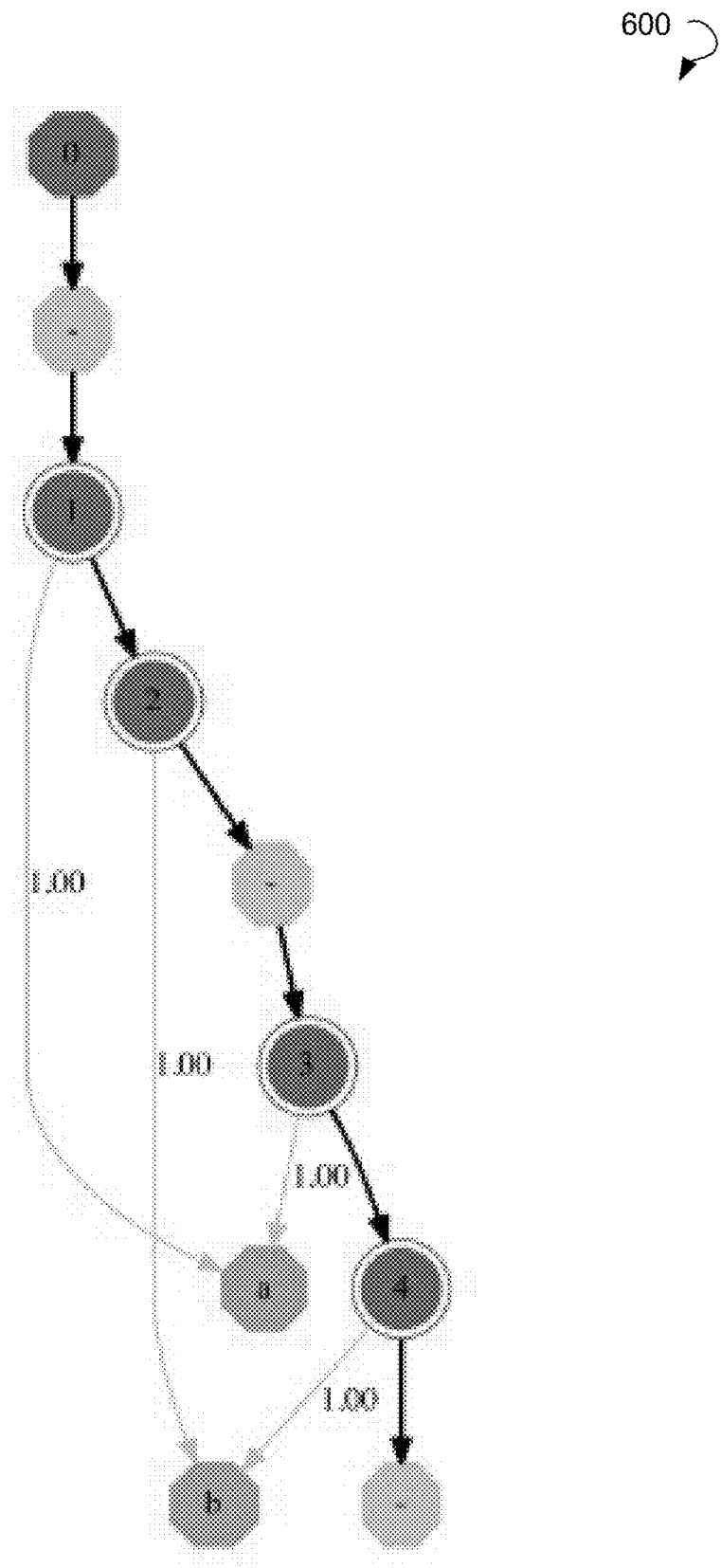
FIG. 6 is a methodology for finding event sequences that can be implemented by the multivariate causation system according to exemplary embodiments of the present technology.

FIG. 6 is a methodology 600 for finding event sequences that can be implemented by the multivariate causation system according to exemplary embodiments of the present technology. In various embodiments, the present technology uses low entropy approaches for causal inference to find event sequences as described below.

1. Causal Variables Discovery.

In some embodiments, the multivariate causation system 110 relies on entropy measures as a causal discovery tool in the sense that a high entropy variable X associated with some particular value of a target variable Y=y cannot be causal. Note that this statement does not imply that a low entropy variable must be a causal variable.

In other words, it is necessary but not sufficient for X to have low entropy in order to be causal for Y=y.

For example, imagine that the proposed causal variable X describes what kind of drink you take before going to sleep, and the target variable Y describing the sleep quality. Fixing Y to be a "good quality rest", the worse scenario in terms of causality association is when X is realized to the values "vodka", "milk" or "coffee" exactly one third of the times Y equals "good quality rest", as it seems that the change in X actually does not have an effect on the target variable Y to be set as "good quality rest". In this scenario, the variable X has maximum entropy and we have no motivation to consider X as a cause of having a good quality rest.

In terms of Judea's do notation, $P(y|do(X=x))$ does not change for any x.

2. Causal Dynamical Static Variables Discovery.

Given a set of variable realizations in a temporal sequence with a target variable realization, a low entropy is expressed as similarity between realizations and similarity in the ordering of these realizations.

Output patterns of interest may take the form "watch tv, then take a shower, then play whatever game on your phone and then drink whiskey" whenever you have a good quality rest. It can be said that these sequence of activities have low entropy under the desired output Y="good quality rest", so, this sequence cannot be discarded as a causal activity sequence.

2.1 Pattern Discovery in Activity Sequences.

The multivariate causation system 110 may use the Human Activity Language framework as a universal way to represent any kind of activity at any desired detail level. Assigning a symbol to any particular activity allows the representation of any sequence of activities as a sequence of symbols. It is natural to think about the rules governing a temporal activity pattern, as the grammatical rules used in our everyday language. In fact once this representation is adopted, all formal language theory can be applied.

In some embodiments, additional to Hidden Markov Models, the multivariate causation system 110 is able to implement alternative sequence analysis techniques like Long Short Term Memory recurrent neural networks and the Cortical Learning Algorithm in Hierarchical Temporal Memory theory among others.

2.2 Pattern Extraction from Activity Sequences.

Given a set of activity sequences, a pattern among these sequences should be based only on the subset of activities that are conserved between all sequences. For example, consider the following sequences 'abi', 'agb' and 'eabp'. The presence of the activity 'a' is followed in time for the activity 'b'. Thus, this pattern is called a pattern because it appears consistently among all considered sequences. This pattern can be visualized in the alignment of the activity sequences:

1 2 3 4 5
_ a _ b i
_ a g b _
e a _ b p

In this alignment, gaps (denoted by _) are inserted as necessary in each sequence in order to align the activities 'a' and 'b' in the columns 2 and 4.

Note that this alignment results after the insertion of gaps among the sequences and there are infinite ways of inserting gaps in the sequences. The construction of the alignment depends on deciding in which particular positions are the gaps required to be inserted in the sequences in order to align the same activities.

If the set of possible alignments is denoted by A*, a cost function C: $A^* \rightarrow R$ quantifies how well an alignment is formed. A good alignment (low cost) is the one that contains many columns with the same activity (or very similar activities) among the sequences in each column. A bad alignment (high cost) is an alignment that has columns composed of very different activities and gaps. In this way, C is just the sum of individual column costs. Also, a column cost depends on the direct pairwise cost between activities. If $\Sigma$ is the alphabet of activities, the cost function $c: \Sigma \times \Sigma \rightarrow R$ quantifies the direct similarity between any pair of activities. Additional constrains can be added to the cost function for penalizing activity sequence gaps as needed. Optimization of such cost function can be performed by any general purpose optimization technique, like dynamic programming, Monte Carlo sampling and genetic optimization to name a few.

2.3 Hidden Markov Models from Activity Patterns.

Given a sequence alignment, a Hidden Markov Model (HMM) can be constructed in such a way that each alignment column defines a hidden state, with emission states as the set of activities in such column.

Such HMM represents a model abstracting the consensus behavior of the original set of activity sequences.

For example, consider the set of activity sequences {'uabiabo','labkabj','mabgabd'}. In this case, the sequence pattern found in these sequences is "a followed by b followed by something else, then a followed by b again". This pattern in form of a HMM is depicted in FIG. 6, where states are represented by red circles, connected with activities in orange. Gray nodes represent states that allow any activities. Bold arrows between states represent the temporal flux of states.

2.4 Causality.

Once the multivariate causation system 110 extracts a pattern from a set of activity sequences associated to a particular outcome, additional steps are followed to ensure probabilistic causal relationship between such pattern and target response.

The multivariate causation system 110 considers additional factors in causal dependencies. If a is said to cause b, then it is necessary that:

$P(b|a,k) > P(b|!a,k)$ where k represents any external influence.

For example, the methodology 600 of FIG. 6 for finding event sequences that can be implemented by the multivariate causation system may be an HMM from a set of activity sequences.

Figure 7:
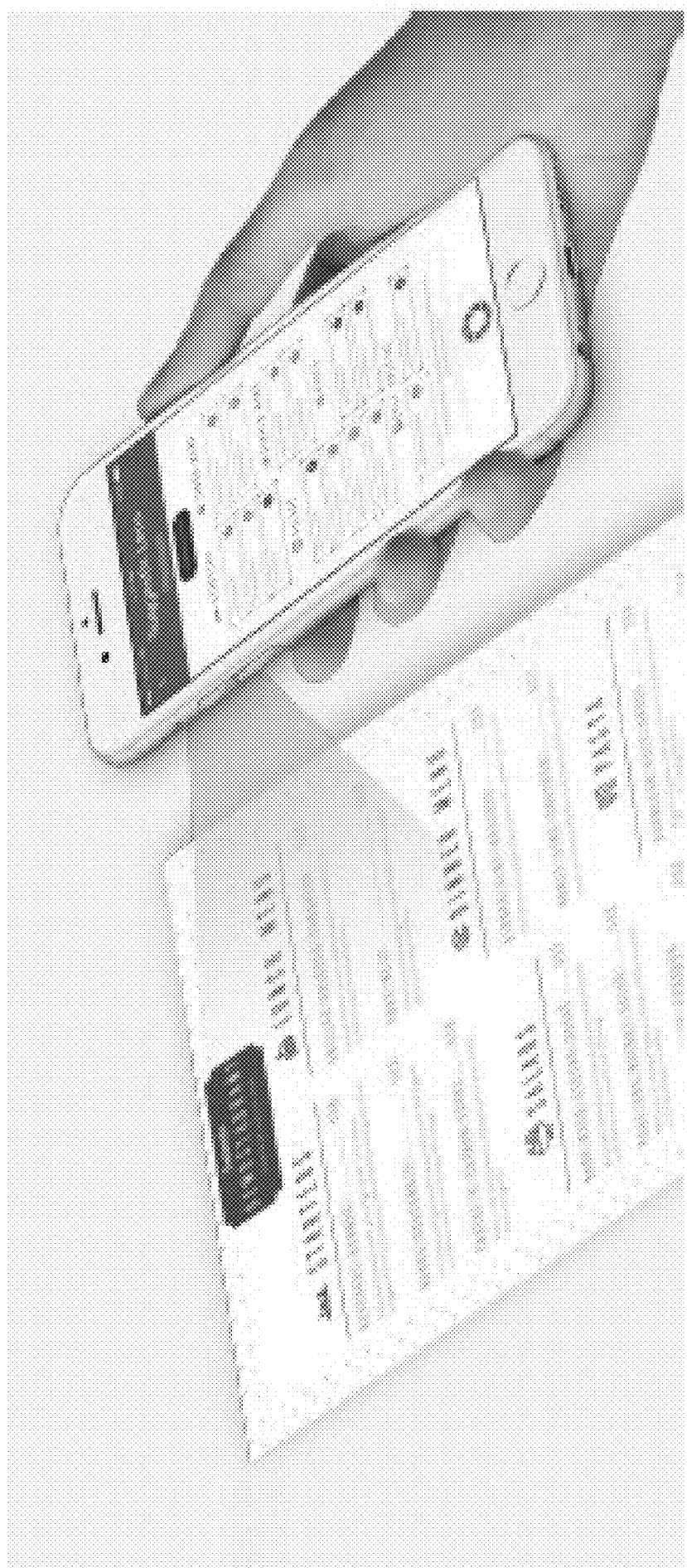
FIG. 7 is a schematic diagram of an augmented reality information overlay enabled by a contextual filtering and adherence scoring system according to exemplary embodiments of the present technology.

FIG. 7 is a schematic diagram 700 of an augmented reality information overlay which exemplifies a decision augmentation delivery method enabled by an adaptive lifestyle and eating program enable by the present technology. In various embodiments, the multivariate causation system 110 along with the contextual filtering and the adherence scoring system 106 are integral parts of the present technology that enable the augmented reality information overlay. According to various embodiments, the augmented reality is on top of a restaurant menu as shown by the schematic diagram 700 in FIG. 7.

According to various embodiments of the present technology, the augmented reality information overlay includes images and video streams from a computer system of the user. For example, augmented reality for each individual restaurant menu uses source images or video streams of the menus that are sent from the computing device of the user. Further, an automated pipeline built to convert these menu images or video streams into augmented reality enabled menus. In some instances, human intervention may be required, but most interactions will include an automated real-time process which is virtually instantaneous. According to various embodiments, enabling augmented reality for each individual restaurant menu uses a fully automated system allowing users a near real-time experience, from the moment a picture is taken or the video stream is turned on, to having the augmented reality experience delivered on their phone. The present technology allows for the overlay of information to include the most up to date suggestions.

Figure 8:
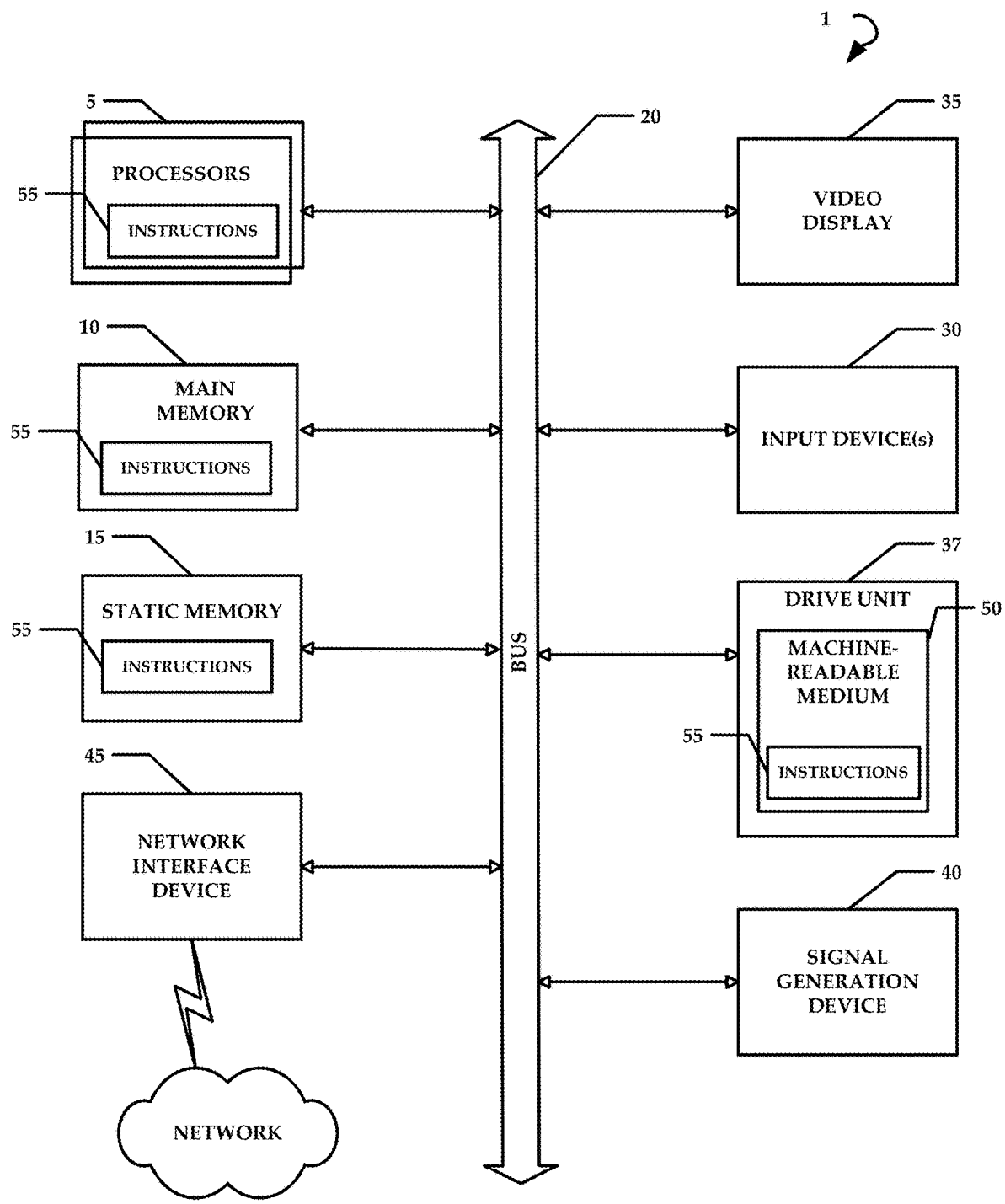
FIG. 8 illustrates a computer system according to exemplary embodiments of the present technology.

FIG. 8 is a diagrammatic representation of an example machine (e.g. computing device 116) in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as an Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alpha-numeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The disk drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated.

The terminology used herein is for the purpose of describing particular embodiments only and is not intended to be limiting of the technology. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that like or analogous elements and/or components, referred to herein, may be identified throughout the drawings with like reference characters. It will be further understood that several of the figures are merely schematic representations of the present technology. As such, some of the components may have been distorted from their actual scale for pictorial clarity.

The flowchart and block diagrams in the Figures illustrate the architecture, functionality, and operation of possible implementations of systems, methods and computer program products according to various embodiments of the present technology. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It is noted at the outset that the terms "coupled," "connected", "connecting," "electrically connected," etc., are used interchangeably herein to generally refer to the condition of being electrically/electronically connected. Similarly, a first entity is considered to be in "communication" with a second entity (or entities) when the first entity electrically sends and/or receives (whether through wireline or wireless means) information signals (whether containing data information or non-data/control information) to the second entity regardless of the type (analog or digital) of those signals. It is further noted that various figures (including component diagrams) shown and discussed herein are for illustrative purpose only, and are not drawn to scale.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel, or may be performed at different times.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A decision augmentation system, comprising:
   an augmented reality information overlay;
   a ruleset generator system that creates rulesets based on empirical studies;
   a personalized program generation system that applies individualized data of a user to create a personalized lifestyle and eating program for the user based on one or more of the rulesets;
   a passive and active feedback system that provides empirical results of actions and behaviors of the user;
   a multivariate causation system that selectively adjusts the rulesets based on the empirical results of the actions and behaviors of the user; and
   a contextual filtering and adherence scoring system that dynamically selects individualized suggestions based on context of the user and the personalized lifestyle and eating program for the user,
   the contextual filtering and adherence scoring system providing the augmented reality information overlay, the augmented reality information overlay including the individualized suggestions.

2. The decision augmentation system of claim 1, wherein the augmented reality information overlay being a list of the individualized suggestions, the list of the individualized suggestions helping the user in at least one of: selection of restaurant menu items, ingredients, beverages, food products, groceries, supplements, and medication.

3. The decision augmentation system of claim 1, wherein the augmented reality information overlay is at least one of: images and video streams from a computer system of the user.

4. The decision augmentation system of claim 1, wherein the personalized lifestyle and eating program is initially encoded into the rulesets by selecting one or more proven published dietary plans.

5. The decision augmentation system of claim 1, wherein the individualized data is at least one of: personal goals, diet, program selection, preferences, restrictions, lab test results, biomarkers, sensor data, health information, demographics, daily activity, genome, microbiome, environment, and personal information.

6. The decision augmentation system of claim 1, wherein the individualized suggestions include at least one of: activities, food, supplements, and medication.

7. The decision augmentation system of claim 1, wherein the multivariate causation system utilizes at least one: of deep learning and machine learning to analyze information from other similar users to the user, the information from other similar users being at least one: of similar genetics, a similar biomarker, similar lab test results, a similar profile, similar activities, a similar background, and similar clinical data to the user.

8. The decision augmentation system of claim 1, wherein the multivariate causation system receives data from external sensors.

9. The decision augmentation system of claim 8, wherein the external sensors include at least one of: wearable smart glasses, wearable watches, sleep sensors, blood pressure monitors, glucose monitors, insulin pumps, blood pressure sensors, respiration monitors, pulse-oximetry meters, and heart rate meters.

10. The decision augmentation system of claim 8, wherein the external sensors provide data to a third-party, the third-party being at least one of: a proprietary system and a health professional.

11. A decision augmentation system, comprising:
    an augmented reality information overlay;
    a ruleset generator system that creates rulesets based on empirical studies;
    a personalized program generation system that applies individualized data of a user to create a personalized lifestyle and eating program for the user based on one or more of the rulesets;
    a passive and active feedback system that provides empirical results of actions and behaviors of the user;
    a multivariate causation system that selectively adjusts the rulesets based on the empirical results of the actions and behaviors of the user, the multivariate causation system utilizing machine learning to analyze information of other similar users, the information of the other similar users being similar data to the user; and
    a contextual filtering and adherence scoring system that dynamically selects individualized suggestions based on context of the user and the personalized lifestyle and eating program for the user,
    the contextual filtering and adherence scoring system providing the augmented reality information overlay, the augmented reality information overlay including the individualized suggestions.

12. The decision augmentation system of claim 11, wherein the information of the other similar users includes at least one of: similar genetics, similar biomarkers, similar lab test results, a similar profile, similar activities, a similar background, and similar clinical data.

13. The decision augmentation system of claim 12, wherein the multivariate causation system further selectively adjusts the rulesets based on a goal of the user.

14. The decision augmentation system of claim 13, wherein the multivariate causation system extracts patterns based on the utilizing of machine learning to analyze the information of the other similar users.

15. The decision augmentation system of claim 14, wherein the patterns include sequences, the sequences being related to the goal of the user.

16. The decision augmentation system of claim 15, wherein the sequences include at least one of: exercise activities, food selections, and events.

17. The decision augmentation system of claim 15, wherein the multivariate causation system selectively modifies the rulesets based on the patterns.

18. The decision augmentation system of claim 14, wherein the multivariate causation system selectively adjusts the rulesets based on an expected outcome, the expected outcome based on the patterns.

19. A decision augmentation method, the method comprising:
generating an augmented reality information overlay;
creating rulesets, using a ruleset generator system, based on empirical studies;
applying, using a personalized program generation system, individualized data of a user to create a personalized lifestyle and eating program for the user based on one or more of the rulesets;
providing, using a passive and active feedback system, empirical results of actions and behaviors of the user;
selectively adjusting, using a multivariate causation system, the rulesets based on the empirical results of the actions and behaviors of the user, the multivariate causation system utilizing machine learning to analyze information of other similar users, the information of the other similar users being similar data to the user;
dynamically selecting, using a contextual filtering and adherence scoring system, individualized suggestions based on context of the user and the personalized lifestyle and eating program for the user; and
providing, using the contextual filtering and adherence scoring system, the augmented reality information overlay, the augmented reality information overlay including the individualized suggestions.

20. The decision augmentation method of claim 19, wherein the augmented reality information overlay is a video stream from a computer system of the user.

* * * * *